United States Patent [19]
Tu et al.

[11] Patent Number: 6,123,703
[45] Date of Patent: Sep. 26, 2000

[54] ABLATION CATHETER AND METHODS FOR TREATING TISSUES

[76] Inventors: Lily Chen Tu; Hosheng Tu, both of 2151 Palermo, Tustin, Calif. 92782

[21] Appl. No.: 09/157,360

[22] Filed: Sep. 19, 1998

[51] Int. Cl.⁷ .................................................. A61B 18/18
[52] U.S. Cl. ............................ 606/41; 607/101; 606/49
[58] Field of Search ........................... 606/41, 42, 45, 606/49; 607/98–102, 116

[56] References Cited

U.S. PATENT DOCUMENTS

| | | | |
|---|---|---|---|
| 5,100,423 | 3/1992 | Fearnot | 606/159 |
| 5,344,435 | 9/1994 | Turner et al. | 607/101 |
| 5,370,677 | 12/1994 | Rudie et al. | 607/101 |
| 5,738,683 | 4/1998 | Osypka | 606/47 |
| 5,860,974 | 1/1999 | Abele | 606/41 |

*Primary Examiner*—Linda C. M. Dvorak
*Assistant Examiner*—Roy Gibson

[57] ABSTRACT

An ablation catheter system for treating tissues or atherosclerotic tissues of a patient having a retractable metallic element means comprising a deployable close loop with a running noose at its end, the ablation catheter providing RF therapy to the tissues through the retractable metallic elements means and optional fluid medicine for therapeutic purposes.

19 Claims, 9 Drawing Sheets

ABLATION CATHETER AND METHODS FOR TREATING TISSUES

The present invention generally relates to improved medical apparatus and methods for treating vascular tissues, and more particularly, to such an ablation catheter and methods for treating atherosclerotic tissues in a patient by delivering therapeutic RF energy through a retractable metallic element to the specific lesion sites.

BACKGROUND OF THE INVENTION

An artery is one of the tube-shaped blood vessels that carries blood away from the heart to the body's tissues and organs. An artery is made up of an outer fibrous layer, a smooth muscle layer, a connecting tissue layer, and the inner lining cells. If arterial walls become hardened due to the accumulation of fatty substances, then blood flow can be diminished. Hardening of the arteries, or loss of vessel elasticity, is termed arteriosclerosis while fatty deposit build-up is termed atherosclerosis. Atherosclerosis and its complications are a major cause of death in the United States. Heart and brain diseases are often the direct result of this accumulation of fatty substances that impair the arteries' ability to nourish vital body organs.

Balloon angioplasty is a nonsurgical method of clearing coronary and other arteries, blocked by atherosclerotic plaque, fibrous and fatty deposits on the walls of arteries. The use of a balloon catheter to treat stenosis or narrowing within various parts of the human body is well known. A catheter with a balloon-like tip is threaded up from the arm or groin through the artery until it reaches the blocked area. The balloon is then inflated, flattening the plaque and increasing the diameter of the blood vessel opening. The arterial passage is thus widened. As a result of enlarging the hardened plaque, cracks occur within the plaque to expose the underlying fresh tissue or damaged cells to the blood stream.

In a typical procedure, for example, to dilate a stenosis in the coronary arteries, a relatively large guiding catheter is inserted into the patient's arterial system in the groin. The guiding catheter is then advanced through the arteries to a location near the patient's heart. A small wire guide is then inserted into the guiding catheter and advanced to the distal end of the guiding catheter, at which point it is steered to extend through the stenosis in the coronary arteries. A balloon catheter is then advanced over the wire guide until the deflated balloon lies across the stenosis. A working fluid is then pumped through the balloon catheter, thereby inflating the balloon and dilating the passage through the stenosis.

There are limitations, however, to this technique's application, depending on the extent of the disease, the blood flow through the artery, and the part of the anatomy and the particular vessels involved. Plaque build-up and/or severe re-stenosis recurrence within 6 months is up to 30–40 percent of those treated. Balloon angioplasty can only be characterized as a moderate-success procedure. Recently, a newer technique of inserting a metallic stenting element is used to permanently maintain the walls of the vessel treated at its extended opening state. Vascular stents are tiny mesh tubes made of stainless steel or other metals and are used by heart surgeons to prop open the weak inner walls of diseased arteries. They are often used in conjunction with balloon angioplasty to prevent restenosis after the clogged arteries are treated. Stenting technique reduces the probability of restenosis; however, the success rate is still sub-optimal. It was reported that up to 25% restenosis occurs in stent implantation procedures. The underlying fresh tissue or denuded cells after balloon angioplasty procedures still pose as a precursor for vessel reclosures or angio-spasm.

When a clogged artery is widened, the plaque is broken up and the underlying fresh collagen or damaged endothelium is exposed to the blood flow. Collagen has a pro-thrombotic property that is part of the body healing process. Unless the collagen or the damaged endothelium is passivated or modulated, the chances for blood vessel clotting as well as restenosis exist. Moderate heat is known to tighten and shrink the collagen tissue as illustrated in U.S. Pat. No. 5,456,662 and U.S. Pat. No. 5,546,954. It is also clinically verified that thermal energy is capable of denaturing the tissue and modulating the collagenous molecules in such a way that treated tissue becomes more resilient ("The Next Wave in Minimally Invasive Surgery" MD&DI pp. 36–44, August 1998). Therefore, it becomes imperative to post-treat vessels walls after the walls are treated with angioplasty procedures.

One method of reducing the size of cellular tissues in situ has been used in the treatment of many diseases, or as an adjunct to surgical removal procedures. This method applies appropriate heat to the tissues, and causes them to shrink and tighten. It can be performed on a minimal invasive fashion, which is often less traumatic than surgical procedures and may be the only alternative method, wherein other procedures are unsafe or ineffective. Ablative treatment apparatus have an advantage because of the use of a therapeutic energy that is rapidly dissipated and reduced to a non-destructive level by conduction and convection, to other natural processes.

RF therapeutic protocol has been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after first locating the tissue sites for treatment. Radiofrequency current or energy, when coupled with a temperature control mechanism, can be supplied precisely to the catheter-to-tissues contact site to obtain the desired temperature for treating a tissue.

It becomes a clinical need to provide a stentless metal-to-tissue contact surface for applying thermal energy to the tissue needed for treatment or modulation. In the case of angioplasty alone, the enlarged blood vessel still needs certain metallic contact surface for delivering the RF thermal energy to the denuded collagen or damaged endothelium. A stentless metallic element, which is also known as a retractable no-stent metallic element, is useful in this case to shrink and tighten the target tissue. The stentless metallic element can be a part of the angioplasty balloon to effectively treat the target tissues. Therefore, there is a need for an improved medical catheter having the capability to effectively contact the inner walls of a tubular vessel using the radiofrequency energy to treat an enlarged artery or other tissues, such as esophagus, larynx, uterus, urethra and the like.

SUMMARY OF THE INVENTION

In general, it is an object of the present invention to provide a method and an improved medical ablation catheter for generating heat, to treat the vascular vessels due to atherosclerosis, or other tissues, such as intestine, colon, uterus, bile duct, uterine tube, and the like. It is another object of the present invention to provide a method and a catheter for monitoring the temperature of the ablated tissue by at least one temperature sensor, and to control the temperature by utilizing a temperature control mechanism and/or algorithm. The location of the at least one temperature sensor means is preferably at close proximity of the electrode means of the ablation apparatus. It is still another object of this invention to provide a method and an apparatus for treating vascular walls, or tubular cellular tissues in a patient by applying RF current to a retractable metallic element and subsequently to the underlying tissues. The retractable metallic element in this invention includes, but not limited to, a spiral coil, a loop, a ring, a coiled ring, a meshed ring, a coil, a long line with a running noose at one end (a lasso-type ring) or other appropriate form.

Briefly, heat is generated by supplying a suitable energy source to an apparatus, which is comprised of at least one electrode means, in contact with the body tissues through a retractable metallic element. The "retractable metallic element" in this invention constitutes the delivery means for the electrode means and is used to contact the target tissues for subsequent ablation therapy. In one embodiment, the retractable metallic element is preferably made of high strength, high elastic metals, such as stainless steel or Nitinol. A suitable energy source may consist of radiofrequency energy, microwave energy, ultrasonic energy, alternating current energy, or laser energy. The energy can be applied to the retractable metallic element and subsequently to the atherosclerosis site, vascular walls, or cellular tissues through the electrode means. A DIP (dispersive indifferent pad) type pad or electrode, that contacts the patient, is connected to the Indifferent Electrode Connector on the RF generator. Therefore, the RF energy delivery becomes effective when a close circuit from a RF generator through a patient and returning to the RF generator is formed. When using an alternating current outlet, the generator should be grounded to avoid electrical interference. Heat is controlled by the power of the RF energy delivered and by the delivery duration. The standard RF energy generator means and its applications through the electrode means, to a patient are well known for those who are skilled in the art.

In one embodiment, the apparatus comprises a deployable electrode means that comprises at least one retractable metallic element. In a preferred embodiment, the retractable metallic element is a spiral coil wire having a running noose at one end of the coil to form a complete circle. Resilience and semi-compressibility becomes the property of the coil wire electrode to ultimately deploy to its full extent. The deployed metallic element is to intimately contact an inner wall of a tubular organ, such as an enlarged artery or a bile duct at appropriate contact points; and subsequently the metallic element becomes an electrode means because the metallic element contacts the tissues underlying it, and because the electrode means is connected to an external RF current generating means through an electrical conductor. In the case of a retractable metallic element inside a tubular body vessel, the retractable metallic element is preshaped and extends to its maximum distance circumferentially to contact the target tissue. The retractable metallic element is semi-compressible so that when the deployed metallic element is pressed against the tissue, an appropriate pressure is exerted onto the tissue to ensure intimate contact when applying the RF energy therapy.

In one further embodiment, the ablation catheter comprises a fluid duct within the inner catheter, the fluid duct having a proximal end and a distal end. The distal end of the fluid duct is connected to the retractable metallic element means, wherein the fluid is supplied to the retractable metallic element means. The retractable metallic element is either made of a porous metal or has a plurality of tiny openings. Said openings on the retractable metallic element preferably face the outermost side of the loop. The fluid is selected from the group consisting of a serotonin antagonist, a cyclooxygenase inhibitor, an endothelin antagonist, an ATP-sensitive $K^+$ channel antagonist, a $Ca^{2+}$ channel antagonist, a nitric oxide donor, an anti-thrombin agent, a glycoprotein IIb/IIIa receptor blocker, a PKC inhibitor and a protein tyrosine kinase inhibitor. The fluid has a general therapeutic purposes for perioperatively inhibiting a variety of pain, inflammation, spasm and restenosis processes. The fluid preferably includes multiple pain and inflammation inhibitory agents and spasm inhibitory agents at dilute concentration in a physiologic carrier, such as saline or lactated Ringer's solution.

To further simplify the apparatus construction and procedures, a balloon angioplasty catheter, either a single-operator rapid exchange type or over-the-wire type, may incorporate the retractable metallic element means having a RF ablation capability as a portion of said balloon catheter.

The method and its ablation catheter system of the present invention has several significant advantages over other known systems or techniques to treat the atherosclerosis or enlarged tissues. In particular, the catheter system comprising at least one retractable metallic element using RF energy as a heat source results in a more efficient therapeutic effect, which is highly desirable in its intended application on the atherosclerotic tissues.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 6, what is shown is an embodiment of the ablation catheter system, comprising applying radiofrequency energy and optionally applying a therapeutic fluid to treat the atherosclerotic vascular vessels, or other tubular cellular tissues of a patient through a retractable metallic element means.

Figure 1:
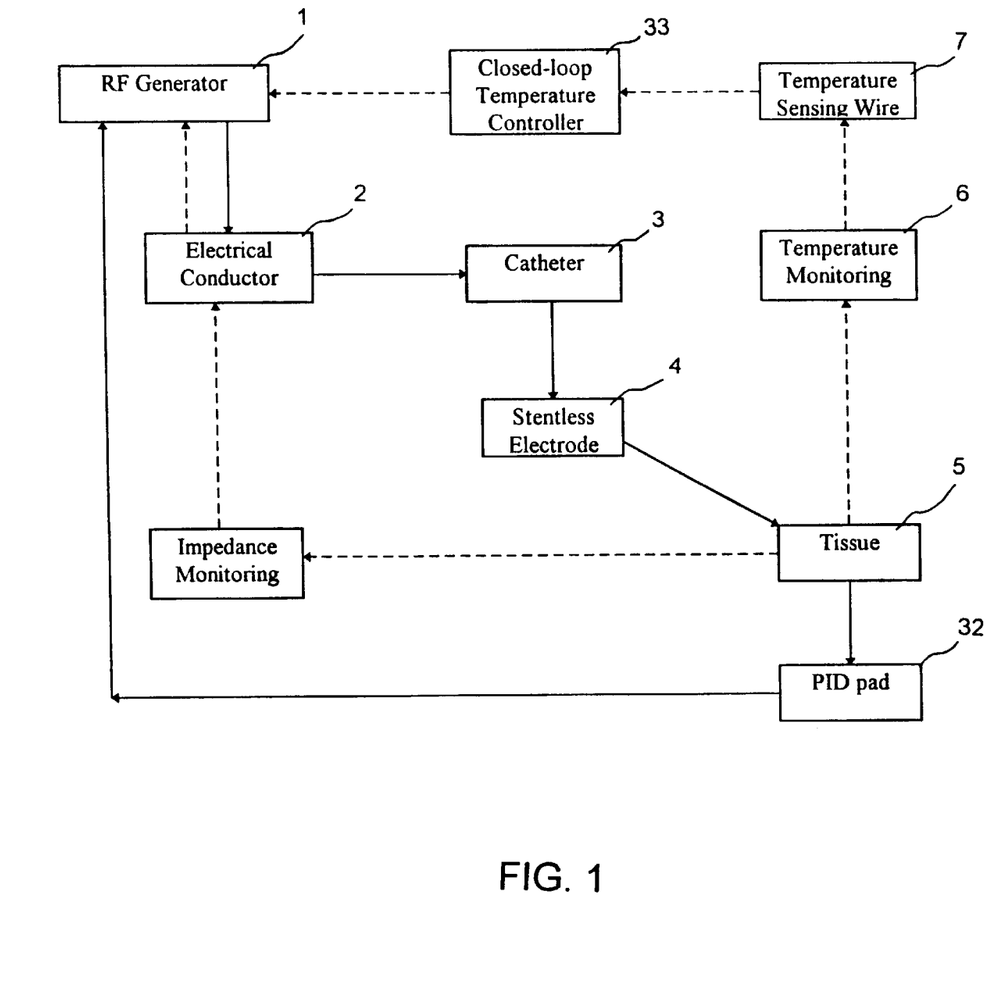
FIG. 1 is a schematic diagram of a RF treatment method in relation to the tissues through an electrode means comprising a retractable metallic element means in a patient.

FIG. 1 shows a schematic diagram of a RF treatment method in relation to the tissues or atherosclerotic tissues through a stentless retractable metallic electrode means in a patient. A RF current generator 1 is connected to a catheter or an ablation apparatus 3 through an electrical conductor 2. A stentless electrode 4 of the catheter 3 is to contact the tissue 5 of a patient through a retractable metallic element means when the catheter is deployed. The deployed retractable metallic element means is in close contact with the underlying tissue 5. A DIP (dispersive indifferent pad) type pad 32, that contacts the patient, is connected to the Indifferent Electrode Connector on the RF generator 1. Therefore, the RF current delivery becomes effective when a close circuit from a RF generator through a patient and returning to the RF generator is formed. Impedance measured from the tissue contact is to ensure good tissue contact for ablation, otherwise the RF power is cutoff when the impedance is unreasonably high. At least one temperature sensor 6 is used to measure the tissue temperature and is relayed through a temperature sensing wire 7 and a closed-loop temperature controller 33 for controlling the ablative energy delivery. Heat is controlled by the current of the RF energy delivered and by the delivery duration.

Figure 2:
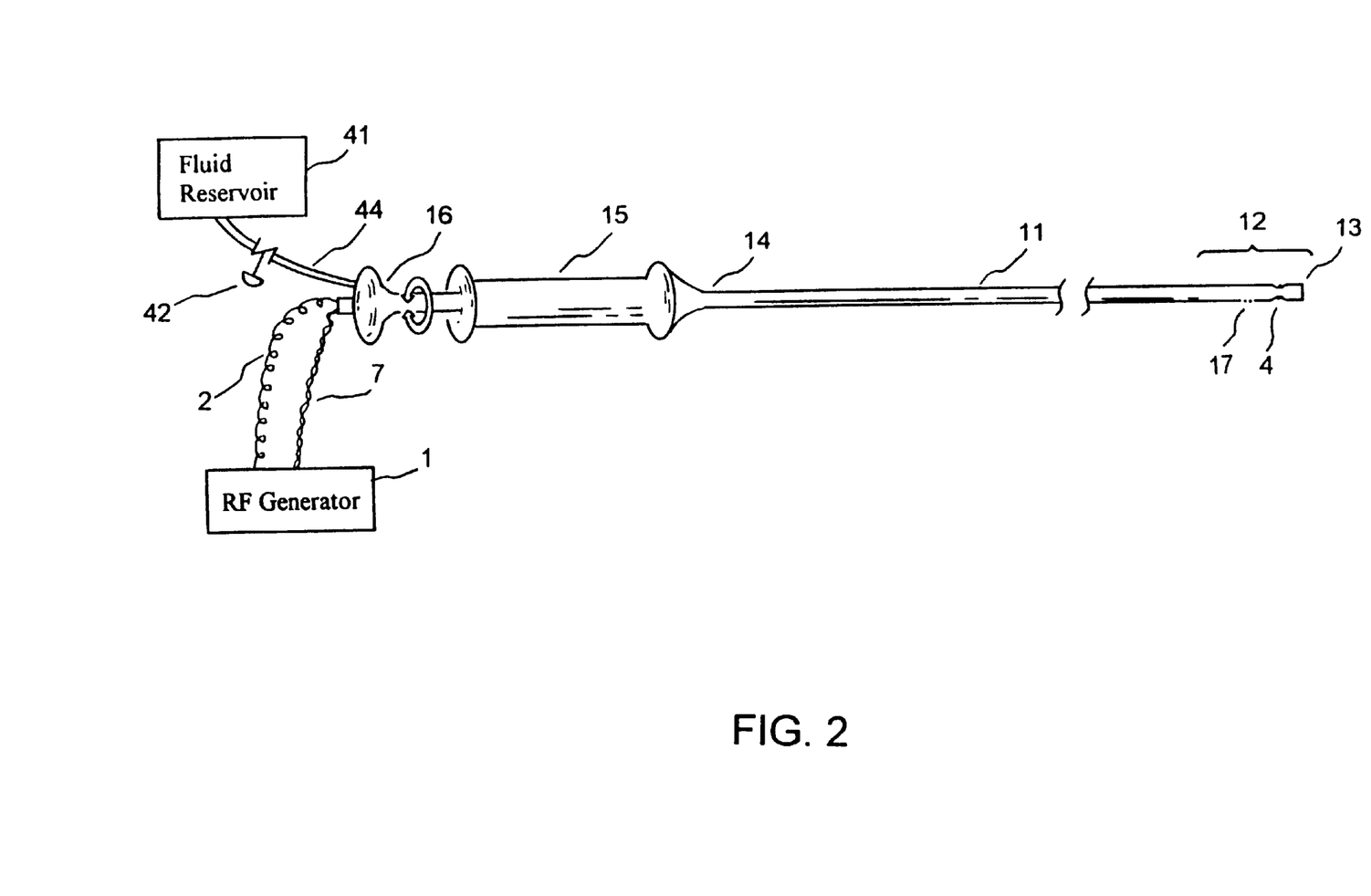
FIG. 2 is an overall view of an ablation catheter having a retractable metallic element means, a RF generator, and an optional fluid irrigation means constructed in accordance to the principles of the present invention.

As shown in FIG. 2, an ablation catheter system comprises a delivery catheter 11. The delivery catheter has a distal section 12, a distal end 13, a proximal end 14, and at least one lumen 8 extending therebetween, wherein the delivery catheter 11 has an opening 20 at the distal section 12. A handle 15 is attached to the proximal end 14 of the delivery catheter 11, wherein the handle 15 has a cavity. An inner catheter 21 is located within the at least one lumen 8 of the delivery catheter 11. The inner catheter 21 has a tip section, a distal end 22 and a proximal end. A retractable metallic element means 4 is mounted on the tip section of the inner catheter 21, wherein the retractable metallic element means 4 folds and wraps onto the tip section of the inner catheter 21, and wherein an electrical conductor 2 is connected to the retractable metallic element means 4. An electrode deployment means 16 is mounted on the handle 15, wherein the electrode deployment means 16 is attached to the proximal end of the inner catheter 21. The ablation catheter system also includes a RF current generating means, wherein the RF current is provided through the electrical conductor 2 to the retractable metallic element means 4.

In one embodiment, the ablation catheter system of the present invention comprises a fluid duct 43 within the inner catheter 21. The fluid duct 43 has a proximal end and a distal end. The distal end of the fluid duct is connected to the retractable metallic element means 4. The fluid is supplied from the fluid reservoir 41 through a controlling valve 42, a fluid conveying duct 44, and the fluid duct 43 to the retractable metallic element means 4. The retractable metallic element means 4 may be either made of a porous metal or has an internal fluid passageway and a plurality of tiny openings for fluid venting.

Figure 3:
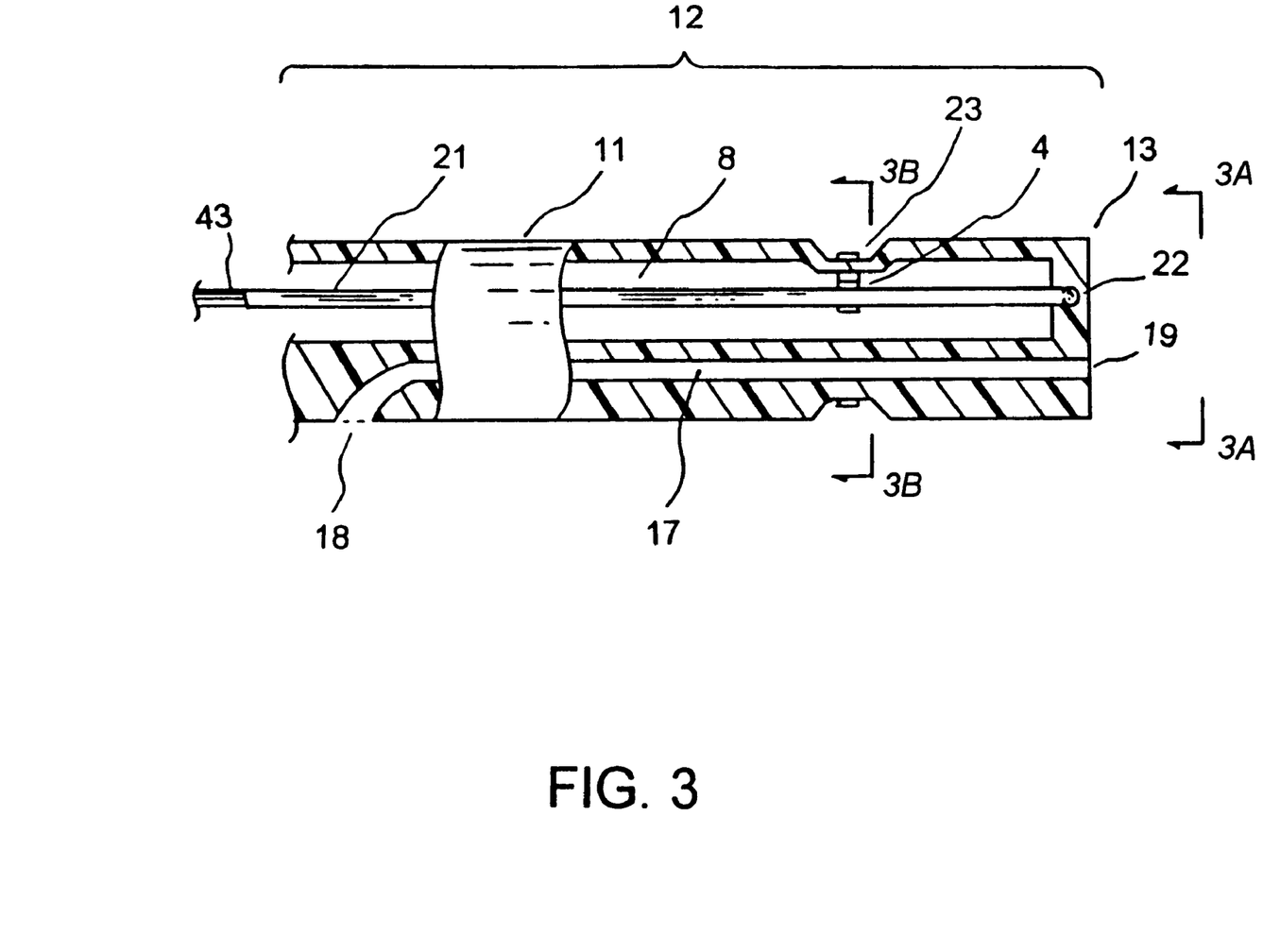
FIG. 3 is a cross-sectional view of the distal end portion of the ablation catheter, having a retractable metallic element means mounted at the tip section of an inner catheter at a non-deployed state.

FIG. 3 shows a cross-sectional view of the distal end portion of the delivery catheter 11, having a retractable metallic element means 4 mounted at the tip section of an inner catheter 21 at a non-deployed state. Under a non-deployed state, the retractable metallic element means 4 is retracted so that the ring-type metallic element wraps around the shaft at the distal section of the delivery catheter 11. The distal end 22 of the inner catheter 21 is loosely suspended within a cavity of the distal end 13 of the delivery catheter 11. There is an optional rapid exchange wire guide shaft 17 for the guide wire insertion. The wire guide shaft 17 has a distal end 19 and a proximal end 18.

Figure 3A:
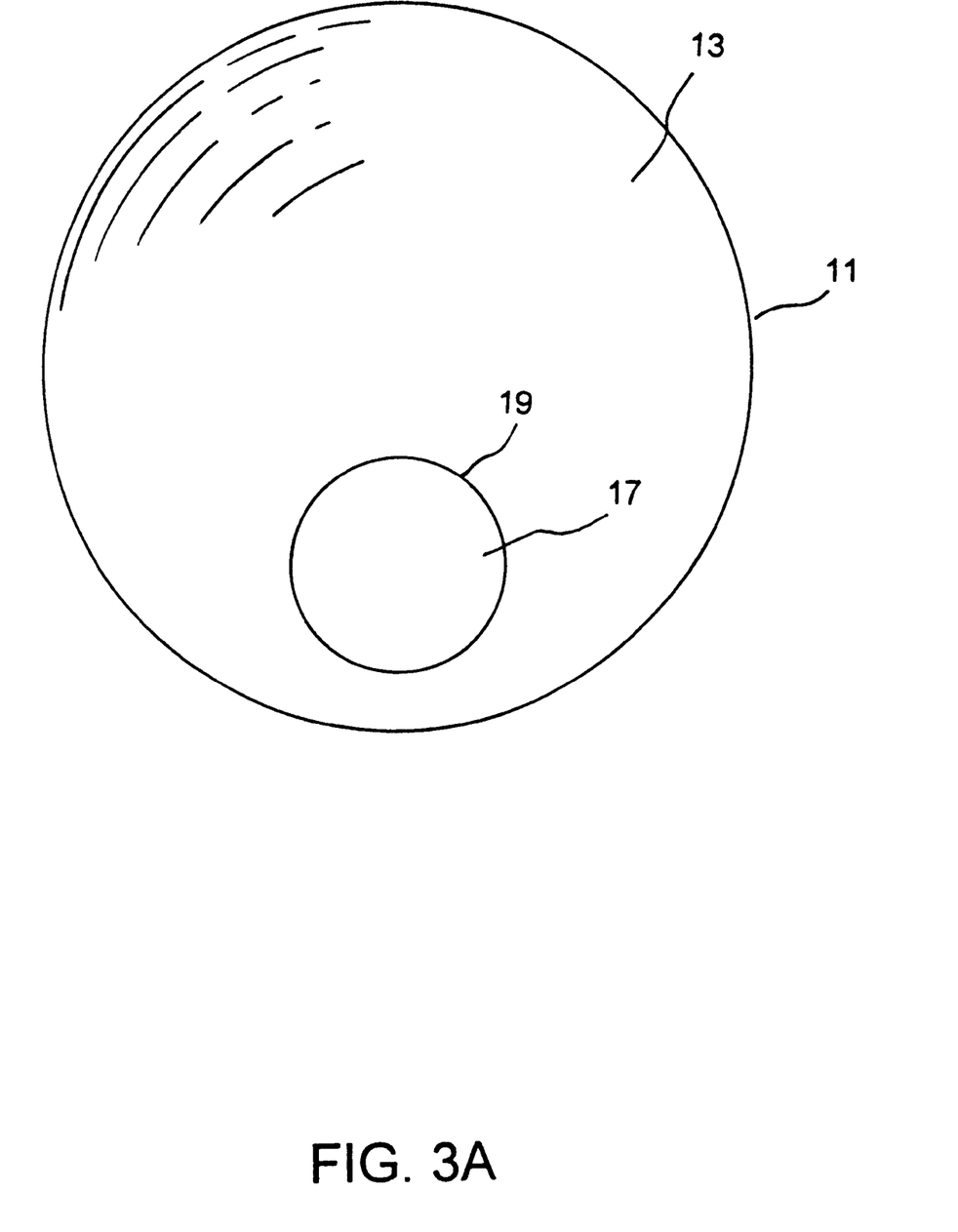
FIG. 3A is a transverse view at section A—A of FIG. 3.
Figure 3B:
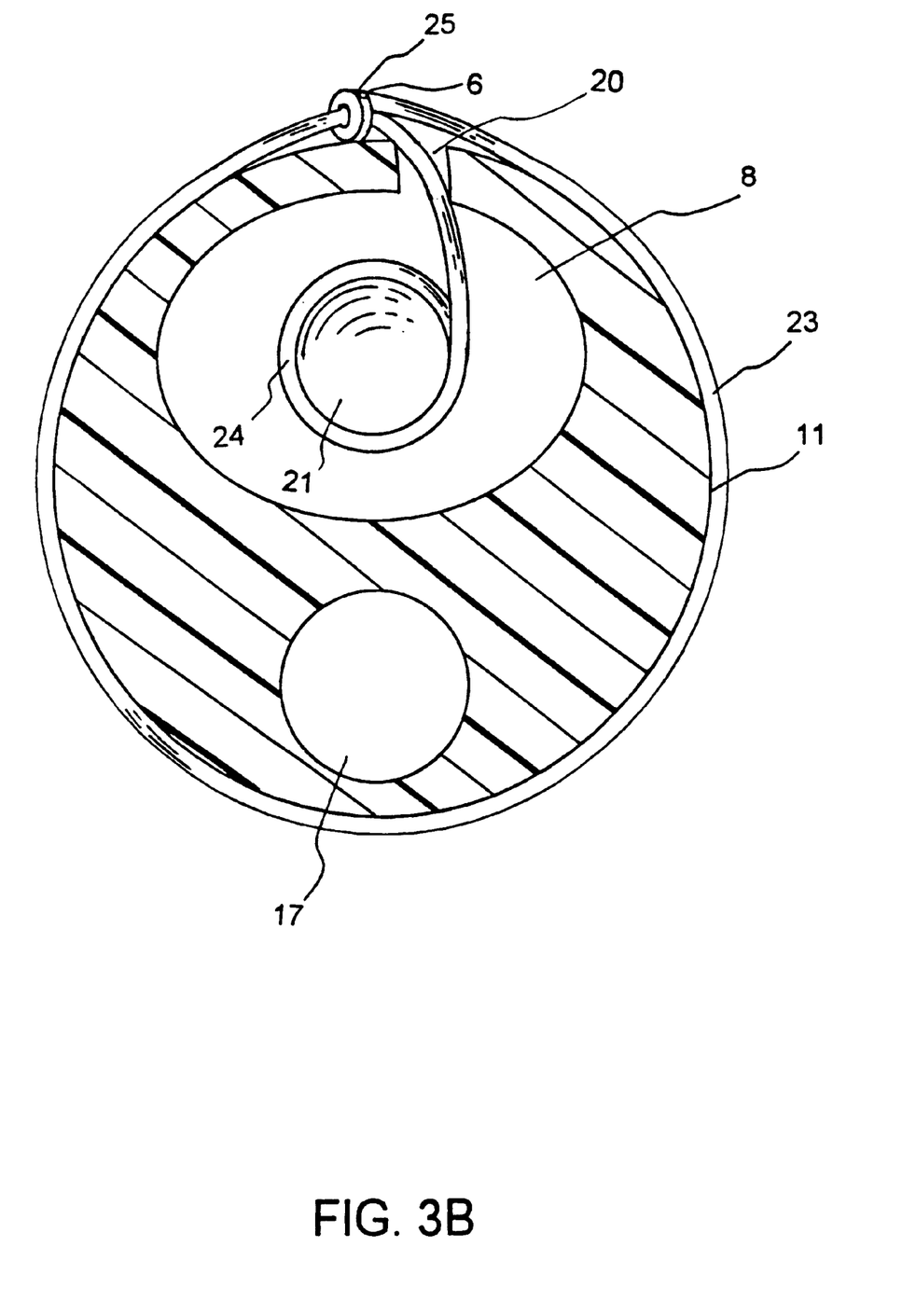
FIG. 3B is a transverse view at section B—B of FIG. 3.

FIG. 3A shows a transverse view at section A—A of FIG. 3. The distal end 13 is part of the delivery catheter 11. FIG. 3B shows a transverse view at section B—B of FIG. 3. The retractable metallic element means 4 comprises a base 24, a loop 23 and a running noose 25 at one end of the loop 23. The retractable metallic element means 4 comprises at least one retractable metallic element. The base 24 wraps onto and around the inner catheter 21. In one embodiment, at least one temperature sensor 6 is located on the loop 23 or on the running noose 25. One example shown is a temperature sensor 6 on the running noose 25, whereby the temperature sensor faces the outermost side. The opening 20 is for the retractable metallic element of the inner catheter 21 to deploy and retract through the delivery catheter 11.

Figure 4:
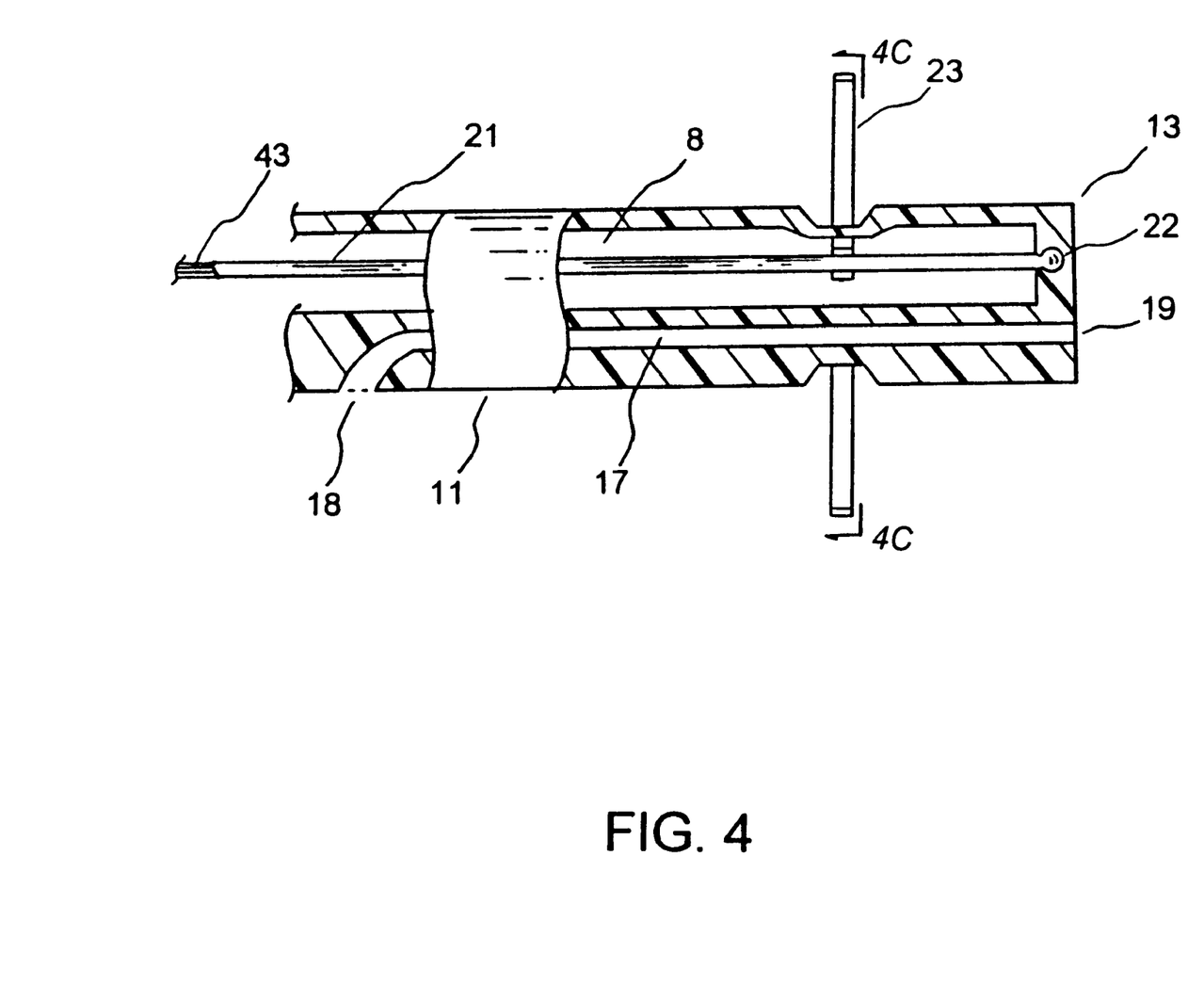
FIG. 4 is a cross-sectional view of the distal end portion of the ablation catheter, having a retractable metallic element means mounted at the tip section of an inner catheter at a deployed state.
Figure 4A:
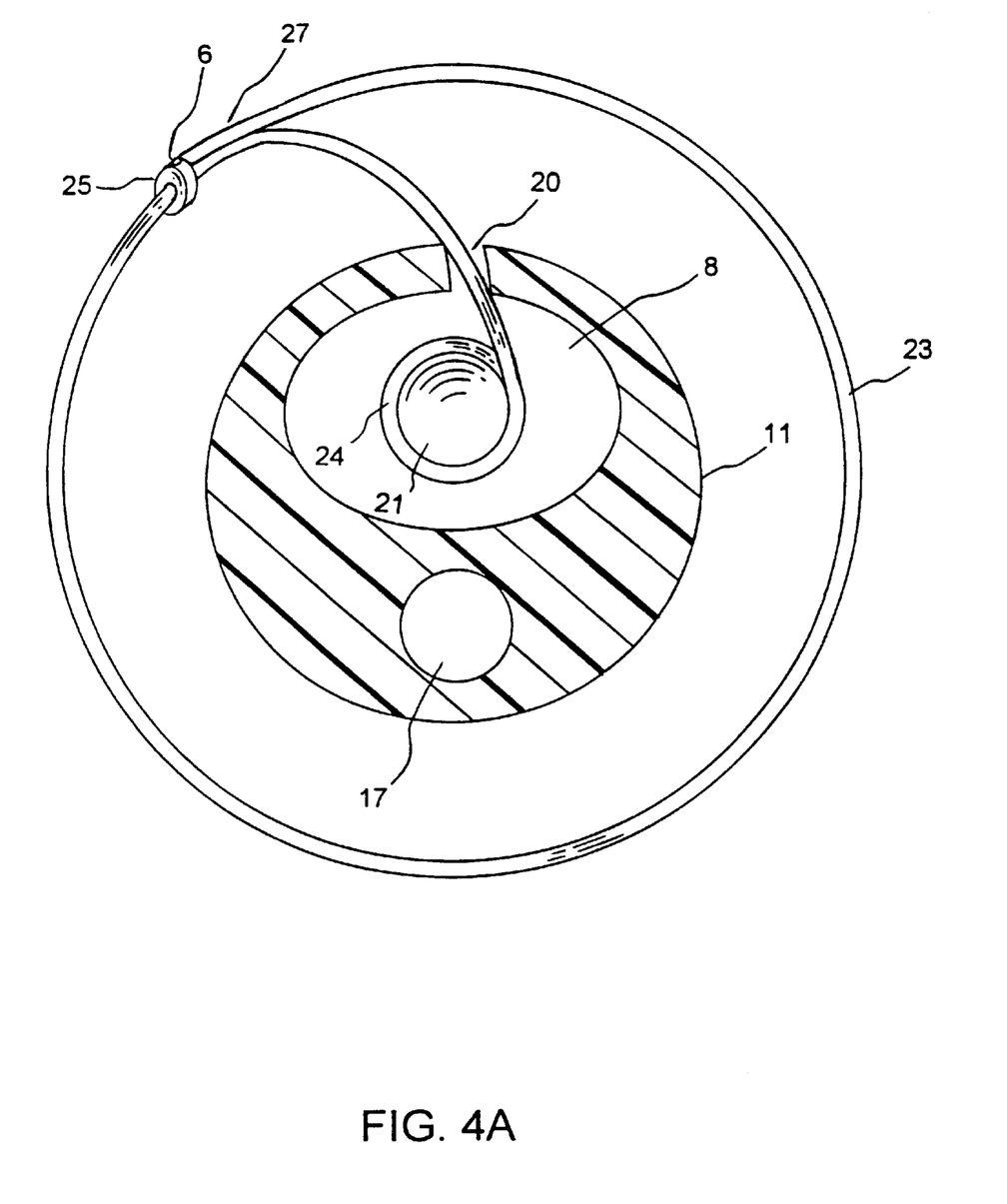
FIG. 4A is a transverse view section C—C of FIG. 4.

FIG. 4 shows a cross-sectional view of the distal end portion of the ablation catheter, having a retractable metallic element means mounted at the tip section of an inner catheter at a deployed state. The deployed loop 23 is part of the retractable metallic element means 4. FIG. 4A shows a transverse view section C—C of FIG. 4. The deployed loop 23 passes through the opening 20 of the delivery catheter 11 and extends radially to its full extent. In one preferred embodiment, the retractable metallic element means 4 comprises at least one loop for one retractable metallic element. The material for the retractable metallic element means is selected from the group consisting of platinum, iridium, gold, silver, stainless steel, Nitinol, or an alloy of their mixtures. In one embodiment, the retractable metallic element means is preshaped and preformed in a close loop fashion and is wrapped around the distal section of the delivery catheter.

In one embodiment, at least one temperature sensing means 6 is disposed at close proximity of the loop 23 of the retractable metallic element means 4. Insulated temperature sensor wire means 7 passes from the temperature sensing means 6, to an external temperature control mechanism 33 through an outlet connector. The RF current delivery is controlled by using the measured temperature from the temperature sensing means 6, through a closed-loop temperature control mechanism and/or algorithm. When the measured temperature rises to a preset high-limit point, the temperature control mechanism sends out a signal to cut off the RF current supply. In a similar manner, when the measured temperature drops to a preset low-limit point, the temperature control mechanism sends out a signal to activate the RF current supply.

Figure 5:
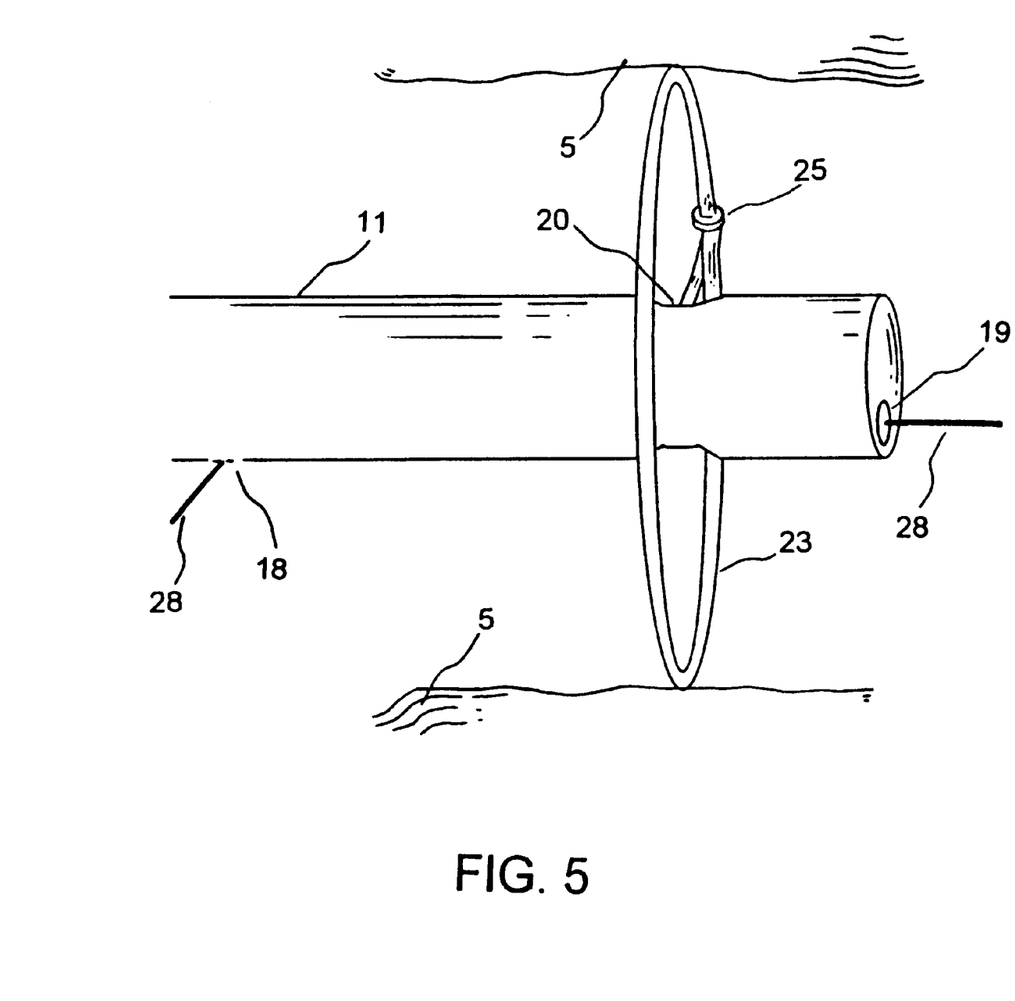
FIG. 5 is a perspective view of the tissue being treated by the ablation catheter having a retractable metallic element means of the present invention.

FIG. 5 shows a perspective view of a tissue 5 or atherosclerotic tissue being treated by the ablation catheter of the present invention. For illustrative purposes, a stenotic artery is enlarged by a balloon catheter in a separate prior procedure. To further passivate or modulate the collagen and/or the denuded endothelium cells, RF current is delivered to the deployed retractable metallic element means 4, whereby the outer surface of the loop 23 of the electrode means contacts the inner wall 5 of the organ at a contact region to treat the atherosclerotic tissues. In another additional embodiment, a guide wire 28 is used to guide the ablation catheter to the target tissue site. The guide wire 28 passes through the wire guide shaft 17 from its proximal end 18 to its distal end 19.

Figure 6:
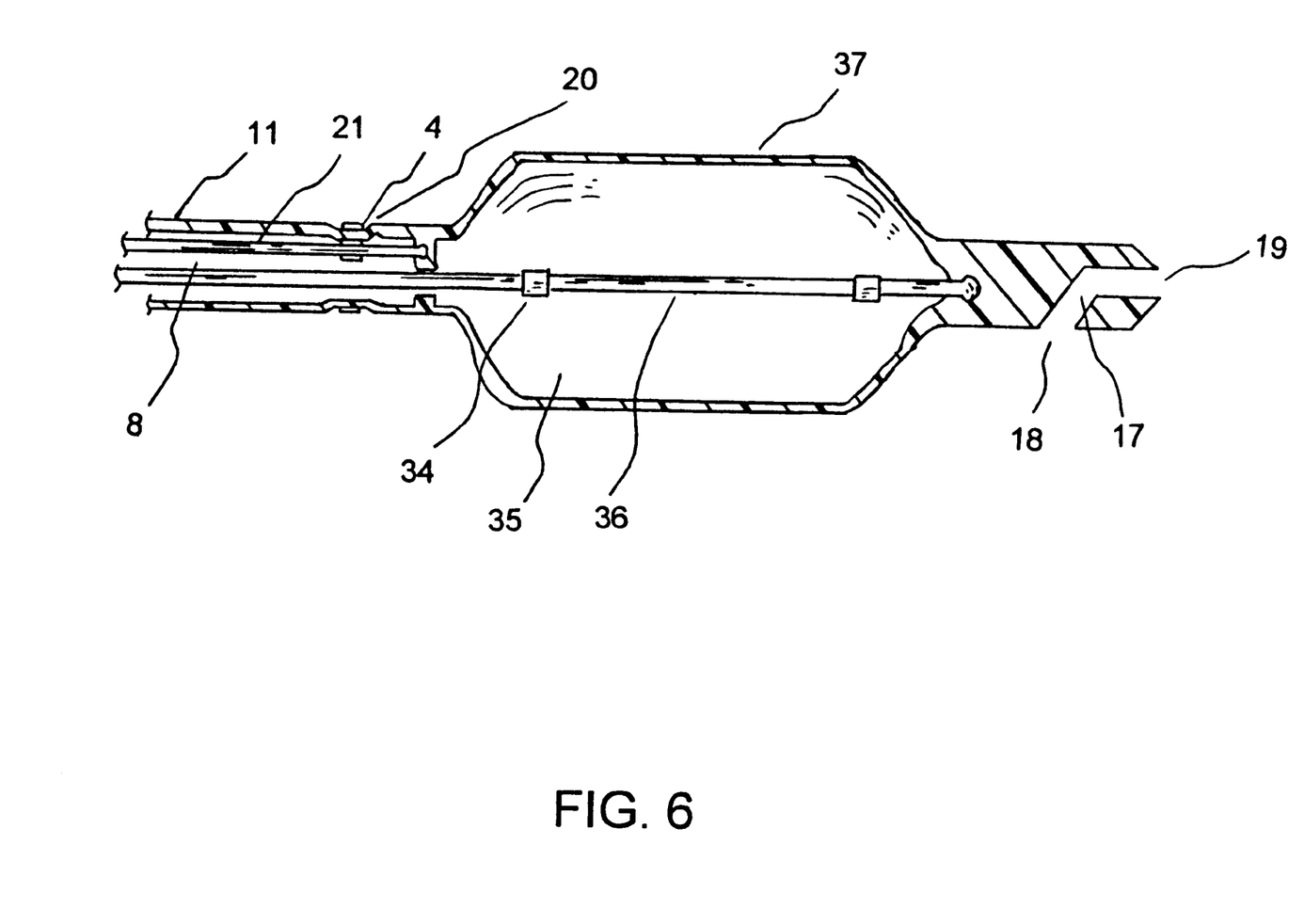
FIG. 6 is a cross-sectional view of the distal end portion of an alternate ablation catheter, having a retractable metallic element means mounted at the tip section of an inner catheter at a non-deployed state, the retractable metallic element means being proximal to the proximal end of a balloon.

FIG. 6 shows a cross-sectional view of the distal end portion of an alternate ablation catheter, having a retractable metallic element means mounted at the tip section of an inner catheter at a non-deployed state, the retractable metallic element means being proximal to the proximal end of a balloon. In another embodiment, a rapid exchange balloon catheter system comprises a delivery catheter 11 having a plurality of lumens 8. The plurality of lumens include an inflation lumen 35, the inflation lumen having a proximal end and a distal end. The delivery catheter 11 has an opening 20 at the distal section. An inflatable balloon 37 has a proximal end and a distal end. A handle (not shown) is attached to the proximal end of the delivery catheter, wherein the handle has a cavity. A wire guide shaft 17 defines a wire guide lumen, the wire guide shaft having a proximal end 18 and a distal end 19, wherein the proximal end of the wire guide shaft is distal to the distal end of the inflatable balloon 37. An inner catheter 21 is located within one of the plurality of lumens 8 of the delivery catheter 11, the inner catheter having a tip section, a distal end and a proximal end. A retractable metallic element means 4 is mounted on the tip section of the inner catheter. The retractable metallic element means has a distal end and a proximal end, wherein the retractable metallic element means folds and wraps onto the tip section of the inner catheter 21. The distal end of the retractable metallic element means is proximal to the proximal end of the inflatable balloon 37. An electrical conductor 2 is connected to the retractable metallic element means 4. An element deployment means 16 is mounted on the handle, wherein the element deployment means is attached to the proximal end of the inner catheter 21. A catheter tip having proximal and distal ends, wherein the distal end of the inflation lumen 35 opens into and is in communication with an interior of the inflatable balloon 37. The distal end of the inflatable balloon 37 is sealed by the proximal end of the catheter tip, and the wire guide shaft is coupled only to the catheter tip completely distally of the distal end of the inflatable balloon 37. The ablation catheter system also comprises a RF current generator means 1, wherein the RF current is provided through the electrical conductor 2 to the retractable metallic element means 4.

The proximal end 18 of the wire guide shaft 17 is preferably formed at an angle to a transverse axis of the wire guide shaft. The balloon catheter system further comprises a stiffening wire 36 having proximal and distal ends, wherein the stiffening wire extends through the interior of the inflatable balloon 37. The balloon catheter system further comprises at least one radiopaque marker band 34 coupled to the stiffening wire 36. The balloon of the balloon catheter system is made of material selected from the group consisting of polyethylene, cross-linked polyethylene, polyethylene terephthalate, and nylon.

During procedures, the ablation catheter is inserted into the body of a patient through natural opening or a surgical hole. A method for inserting an ablation catheter system in a patient for treating the tissues, the method comprising the steps of: (a) inserting the ablation catheter through a natural opening to the location of the tissue for treatment; (b) deploying the retractable metallic element means of the inner catheter to circumferentially extend the retractable metallic element means, adapted to contact the tissues; and (c) applying RF energy to the retractable metallic element means to effect treatment of the tissues.

The external RF current generator means has the capability to supply RF current by controlling the time, power, and temperature through an optional separate closed-loop temperature control means. The patient is connected to the RF generator means through a DIP electrode to form a closed-loop current system. Therefore, RF current is applied and delivered to the targeted atherosclerosis region, through the electrode means of this invention, the "stentless" electrode means. The radiofrequency energy current in this invention is preferably within the range of 50 to 2,000 kHz. By simultaneously applying RF energy to the electrode and/or by supplying the therapeutic fluid, the atherosclerotic tissue can be treated.

In a particular embodiment, the material for the electrode means of this invention consists of conductive metals such as platinum, iridium, gold, silver, stainless steel, Nitinol, or an alloy of these metals.

From the foregoing description, it should now be appreciated that an ablation catheter system for the tubular organs, atherosclerosis, and the treatment of vascular tissues, comprising a suitable energy source and a fluid therapy has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. An ablation catheter system comprising:
    a delivery catheter having a distal section, a distal end, a proximal end, and at least one lumen extending therebetween, wherein the delivery catheter has at least one opening at the distal section;
    a handle attached to the proximal end of the delivery catheter, wherein the handle has a cavity;
    an inner catheter located within the at least one lumen of the delivery catheter, the inner catheter having a tip section, a distal end and a proximal end;
    a retractable metallic element means mounted on the tip section of the inner catheter, wherein the retractable metallic element means is preshaped and preformed in a close loop fashion and is wrapped around the distal section of the delivery catheter, and wherein an electrical conductor is connected to the retractable metallic element means;
    an electrode deployment means mounted on the handle, wherein the electrode deployment means is attached to the proximal end of the inner catheter; and
    a RF energy generating means, wherein the RF energy is provided through the electrical conductor to the retractable metallic element means.

2. The ablation catheter system of claim 1, wherein the close loop of the retractable metallic element comprises a running noose at one end of the loop.

3. The ablation catheter system of claim 1, wherein the at least one lumen of the delivery catheter has at least one opening at the distal end of the delivery catheter.

4. The ablation catheter system of claim 1, wherein the retractable metallic element means has at least one retractable metallic element.

5. The ablation catheter system as in claim 1 further comprising at least one temperature sensor, wherein the temperature sensor is disposed at close proximity of the retractable metallic element means of the inner catheter.

6. The ablation catheter system as in claim 5 further comprising a temperature control means, wherein the temperature measured from the temperature sensor is relayed to the temperature control means and is adapted to effect the RF energy supply to the ablation catheter system.

7. The ablation catheter system of claim 1, wherein the RF current is within the range of 50 to 2,000 kHz.

8. The ablation catheter system of claim 1, wherein the material for the retractable metallic element means is selected from the group consisting of platinum, iridium, gold, silver, stainless steel, Nitinol, or an alloy of their mixtures.

9. The ablation catheter system of claim 1 further comprising a fluid duct within the inner catheter, the fluid duct having a proximal end and a distal end, the distal end of the fluid duct being connected to the retractable metallic element means, wherein the fluid is supplied to the retractable metallic element means, and wherein the retractable metallic element is made of a porous metal.

10. A rapid exchange balloon catheter system, comprising:
   a delivery catheter having a plurality of lumens, wherein the plurality of lumens include an inflation lumen, the inflation lumen having a proximal end and a distal end, and wherein the delivery catheter has an opening at the distal section;
   an inflatable balloon having a proximal end and a distal end;
   a handle attached to the proximal end of the delivery catheter, wherein the handle has a cavity;
   a wire guide shaft defining a wire guide lumen, the wire guide shaft having a proximal end and a distal end, wherein the proximal end of the wire guide shaft is distal to the distal end of the inflatable balloon;
   an inner catheter located within one of the plurality of lumens of the delivery catheter, the inner catheter having a tip section, a distal end and a proximal end;
   a retractable metallic element means mounted on the tip section of the inner catheter, the retractable metallic element means having a distal end and a proximal end, wherein the retractable metallic element means folds and wraps onto the tip section of the inner catheter, wherein the distal end of the retractable metallic element means is proximal to the proximal end of the inflatable balloon, and wherein an electrical conductor is connected to the retractable metallic element means;
   an element deployment means mounted on the handle, wherein the element deployment means is attached to the proximal end of the inner catheter;
   a catheter tip having proximal and distal ends, wherein the distal end of the inflation lumen opens into and is in communication with an interior of the inflatable balloon, the distal end of the inflatable balloon is sealed by the proximal end of the catheter tip, and the wire guide shaft is coupled only to the catheter tip completely distally of the distal end of the inflatable balloon; and
   a RF current generator means, wherein the RF current is provided through the electrical conductor to the retractable metallic element means.

11. The balloon catheter system of claim 10, wherein the proximal end of the wire guide shaft is formed at an angle to a transverse axis of the wire guide shaft.

12. The balloon catheter system of claim 10, wherein the RF current is in the range of 50 kHz to 2,000 kHz.

13. The balloon catheter system of claim 10, wherein the retractable metallic element means is made of material selected from the group of stainless steel, gold, silver, platinum, iridium and Nitinol.

14. The balloon catheter system of claim 10, further comprising a stiffening wire having proximal and distal ends, wherein the stiffening wire extends through the interior of the inflatable balloon.

15. The balloon catheter system of claim 14, further comprising at least one radiopaque marker band coupled to the stiffening wire.

16. The balloon catheter system of claim 10, wherein the balloon is made of material selected from the group consisting of polyethylene, cross-linked polyethylene, polyethylene terephthalate, and nylon.

17. A method for inserting an ablation catheter system in a patient for treating the tissues, the ablation catheter system comprising a delivery catheter having a distal section, a distal end, a proximal end, and at least one lumen extending therebetween, wherein the delivery catheter has an opening at the distal section; a handle attached to the proximal end of the delivery catheter, wherein the handle has a cavity; an inner catheter located within the at least one lumen of the delivery catheter, the inner catheter having a tip section, a distal end and a proximal end; a retractable metallic element means mounted on the tip section of the inner catheter, wherein the retractable metallic element means is preshaped and preformed in a close loop fashion and is wrapped around the distal section of the delivery catheter, and wherein an electrical conductor is connected to the retractable metallic element means; an electrode deployment means mounted on the handle, wherein the electrode deployment means is attached to the proximal end of the inner catheter; and a RF energy generating means, wherein the RF energy is provided through the electrical conductor to the retractable metallic element means;
the method comprising the steps of:
   (a) inserting the ablation catheter through a natural opening to the location of the tissue for treatment;
   (b) deploying the retractable metallic element means of the inner catheter to circumferentially extend the retractable metallic element means, adapted to contact the tissues; and
   (c) applying RF energy to the retractable metallic element means to effect treatment of the tissues.

18. The method for treating tissues of a patient as in claim 17, the ablation catheter further comprising a fluid duct within the lumen of the inner catheter, the fluid duct having a proximal end and a distal end, the distal end of the fluid duct being connected to the retractable metallic element means, wherein the fluid is supplied to the retractable metallic element means, and wherein the retractable metallic element is made of a porous metal.

19. The method for treating tissues of a patient as in claim 18, wherein the fluid is selected from the group consisting of a serotonin antagonist, a cyclooxygenase inhibitor, an endothelin antagonist, an ATP-sensitive $K^+$ channel antagonist, a $Ca^{2+}$ channel antagonist, a nitric oxide donor, an antithrombin agent, a glycoprotein IIb/IIIa receptor blocker, a PKC inhibitor and a protein tyrosine kinase inhibitor.

* * * * *